United States Patent [19]

Zhevnerov

[11] 4,104,590
[45] Aug. 1, 1978

[54] DIGITAL DEVICE FOR MEASURING INSTANTANEOUS PARAMETER VALUES OF SLOWLY VARYING PROCESSES

[76] Inventor: Sergei Vasilievich Zhevnerov, ulitsa Geroev Sibiryakov, 30, kv. 103, Voronezh, U.S.S.R.

[21] Appl. No.: 746,005

[22] Filed: Nov. 30, 1976

[51] Int. Cl.² .............................................. G01P 3/48
[52] U.S. Cl. .................................... 324/166; 324/186
[58] Field of Search .............. 324/166, 168, 163, 181, 324/186

[56] References Cited

U.S. PATENT DOCUMENTS

| | | | |
|---|---|---|---|
| 3,582,942 | 6/1971 | Carter, Jr. et al. | 324/166 X |
| 3,665,309 | 5/1972 | Sato et al. | 324/186 |
| 3,868,570 | 2/1975 | Kopera, Jr. | 324/166 |
| 3,868,845 | 3/1975 | Shimizu | 324/181 X |
| 3,968,434 | 7/1976 | Dixon et al. | 324/166 |

Primary Examiner—Rudolph V. Rolinec
Assistant Examiner—Vincent J. Sunderdick
Attorney, Agent, or Firm—Lackenbach, Lilling & Siegel

[57] ABSTRACT

A proposed digital device for measuring instantaneous parameter values of slowly varying processes comprises a time-to-voltage converter. The first output of said converter is connected to the control input of a hyperbolic function generator and the second output of said converter is connected to the command input of the hyperbolic function generator. The hyperbolic function generator comprises a controlled pulse generator, with a linear modulation characteristic, and a start-stop circuit. The first input of the start-stop circuit is connected to the output of the controlled pulse generator and its second input is connected to the command input of the hyperbolic function generator. The output of the start-stop circuit, which is the output of the hyperbolic function generator, is connected to a counter-indicator unit. The device of the present invention sharply reduces the measurement and analysis time and makes it possible to connect measuring instruments to a computer. A major advantage of the proposed device is the fact that it presents the results of measurements in the units of the specific parameter being measured.

12 Claims, 29 Drawing Figures

DIGITAL DEVICE FOR MEASURING INSTANTANEOUS PARAMETER VALUES OF SLOWLY VARYING PROCESSES

The present invention relates to electric recording and analysis of slowly changing processes and, more particularly, to a digital device for measuring instantaneous parameter values of slowly varying processes. The device of this invention can be most advantageously used for digitally measuring instantaneous values of the pulse rate of men and animals, the respiration rate of men, and the speeds at which liquid media move through the insides of pipes. The device of the present invention can also perform the functions of a digital electronic speedometer in different types of vehicles and of a digital device for measuring the rheological characteristics of polymers.

In nature and technology, there is a host of quasistationary processes of great duration, whose periods are dynamic values which change slowly and at random. It is often necessary to know the parameters which characterize the dynamics of such processes. The most important parameters that characterize the dynamics of slowly varying processes are the instantaneous speed and frequency values, i.e. the periods of such processes, converted into speed and frequency values. In such cases, the analysis time is determined by the period of the process itself. The most convenient type of measurement is the digital measurement: it being the most suitable for an operator and simplifying the connection to a computer. The major difficulty involved in the digital measurement of instantaneous speed and frequency values is the hyperbolic relationship between the period and the frequency, and the period and the speed, i.e.

$$T = (1/F), T = 1/V,$$

where T is the period of the process;
F is the instantaneous frequency value of the process; and
V is the instantaneous speed value of the process.

The known techniques of digitally measuring speeds and frequencies are inadequate for measuring slowly changing processes because of considerable dynamic errors and the prolonged measuring time.

In measuring parameters of processes with nonstationary periods, the dynamic error value may be commensurable with the result of the measurement, which limits the sphere of application of such methods and the devices intended to carry them out. The circuitries of such devices are far too complicated, and their cost is too high. Such devices comprise nonius analog-digital converters; if the measuring time is sufficiently long, such devices are quite accurate if use is made of the method of successive approximations or the iterative method. Such devices do not make it possible to measure parameters of processes whose periods change at random.

There is known a device for measuring the pulse rate of a patient, which is based upon converting the interval between neighboring input pulses into a voltage and producing a hyperbolic function. The device is not very accurate, because of an inadequate accuracy in reproducing the hyperbolic function. This, in turn, is due to the use of piecewise-linear approximation effected with the aid of diode-resistor circuits. As a result, the measurement scale is not sufficiently linear. Further, the device has a low operating speed, which is due to the fact that the function of the switching means is performed by mechanical relays; another reason for this is the fact that the measurement starts when the second pulse arrives at the measuring circuit, because the first pulse only sets the device into the working state. The device under review is hard to adjust, which is due to the use of an analog functional converter. The device employs stable voltage sources to charge the time-setting capacitors; it should be borne in mind that stringent requirements are imposed upon the temperature and time stability of such capacitors. Discrete readjustment of measuring ranges, which is necessary to ensure the required dynamic range of measurement, calls for replacement of time-setting capacitors, which considerably complicates the use of the device. All the foregoing factors account for a limited sphere of application of this device.

There is further known a digital device intended for measuring infralow frequencies. The device is based upon reproducing the hyperbolic function by means of pulse simulation. The digital frequency meter under review comprises a control unit connected to a subtract counter and a code-frequency converter which is also connected to the subtract counter. The outputs of the subtract counter are connected to the code-frequency converter. Upon the onset of a period $T_x$ being measured, the control unit registers a constant time instant $T_o$ whose duration is less than that of the minimum period measured by the instrument. Then, during the period of time $T_x - T_o$, from the value $N_o = K/T_o$ there is subtracted the number of pulses generated by the code-frequency converter and recurring at a variable frequency. As a result, at the end of the period $T_x$ being measured, the subtract counter has a value which is proportional to the frequency $f_x$ being measured. The device is quite complicated and is incapable of measuring the frequencies of processes whose periods are lesser than $T_o$.

There is also known a device for measuring infralow frequencies with functionally coding time intervals. In order to indicate a parameter which is proportional to the frequency $f_x$, while functionally coding the time interval, it is necessary that the coder should reproduce with time a function which is inverse to the function $T_x = 1/f_x$, i.e.

$$\phi(T_x) = K/T_x,$$

where K is the scale factor.

The device under review comprises a generator whose input is the input of the device, the output of said generator being connected to one of the inputs of a coincidence circuit. The output of the coincidence circuit is connected to a subtract counter whose outputs are electrically coupled via command switches to a programming unit. The programming unit's output is connected to the input of a generator which generates pulses of a variable repetition rate. The output of this generator is connected to the second input of the coincidence circuit. The device under review operates as follows. During the period of time $T_x$, to the input of the subtract counter there are applied pulses from the generator of pulses of a variable repetition rate. The pulse repetition rate is altered by an instruction from the programming unit. The generator of pulses of a variable repetition rate is a high reference frequency divider at whose output the pulse rate is changed at moments of time corresponding to the interpolation points of the curve being approximated. In order to ensure a measuring accuracy better than 1 percent in the frequency measuring range $f_{max}/f_{min} = 10$, the curve has to be divided into 25 portions, which accounts for the complexity of the device. The device is incapable of accurately and monotonously reproducing the function; hence, use is made of piecewise-linear approximation. The accuracy and operating speed of the device are inversely proportional to the dynamic range of measurements.

There is also known a device for digitally measuring instantaneous parameter values of slowly changing processes, comprising a time-to-voltage converter. The counting input of said converter's input command flip-flop is the input of the device. The first output of said converter, which is a leadout of a standard capacitor, is connected to the control input of a hyperbolic function generator and its second output, which is one of the outputs of the input command flip-flop of said converter, is connected to the command input of the hyperbolic function generator the outputs of said hyperbolic function generator being connected to a counter-indicator unit. Both outputs of the command flip-flop are electrically coupled to the leadout of the standard capacitor via charging-discharging circuits.

The device under review operates as follows. To the input of the device there are applied voltage pulses corresponding to the extreme values of the process being analyzed. Upon the arrival of the first pulse, the standard capacitor starts being charged and continues being charged until the arrival at the input of the device of the second pulse which sets a limit to the period being measured. The standard capacitor is charged linearly, so at the moment the second pulse arrives, the standard capacitor registers a voltage level which is proportional to the period being measured. This voltage is applied to one of the inputs of a diode regenerative comparator to whose second input there is connected a second standard capacitor which is charged via a resistor. The charging time constant of the second standard capacitor is selected to be much less than that of the first standard capacitor. Thus across one input of the diode regenerative comparator there is a constant voltage which is proportional to the period being measured and across the second input there is a voltage which is linearly increasing. As soon as the voltage across both inputs of the comparator become equal, at the output counter of the device there is applied an indication pulse, whereby the second standard capacitor is discharged. The process is then repeated. The greater the period of the process being measured, the greater the voltage across the first standard capacitor, the voltage across the second standard capacitor increasing until both voltages are maintained equal during a longer period of time. Thus the frequency at the output of the device is low. The lesser the period of the process being measured, the greater the frequency at the output of the device, which means the functional conversion of the hyperbolic function.

The device under review does not provide sufficient accuracy in measuring instantaneous frequency values of slowly changing processes within the range of frequencies being measured $f_{max}/f_{min} = 10$. The temperature stability of the device is low. Another disadvantage of the device lies in the fact that the hyperbolic function generator is built around a diode regenerative comparator whose self-oscillation frequency is relatively low, while periodically comparing voltages. This limits the sphere of application of the device, as far as the measurement of instantaneous values of parameters having great absolute values is concerned. The presence of electromechanical relays, which perform the functions of charging and discharging switches of the capacitors, reduces the operating speed and reliability of the device.

It is an object of the present invention to provide a digital device for measuring instantaneous parameter values of slowly changing processes, which can operate within a sufficiently broad dynamic range, with a ratio between the maximum and minimum frequencies of the process of more than 10.

It is another object of the invention to provide a device having a simple circuitry and a measuring accuracy over the entire range of measurements better than one percent.

It is still another object of the invention to provide a device which can digitally measure instantaneous values of parameters of slowly changing processes, which possess great absolute values.

The foregoing objects are attained by providing a device for digitally measuring parameter values of slowly varying processes, comprising a time-to-voltage converter having an input command flip-flop whose counting input is the input of the device, a first output of said converter, which is a leadout of a standard capacitor, being connected to a control input of a hyperbolic function generator and the converter's second input, which is one of the outputs of said input command flip-flop of said converter, being connected to a command input of the hyperbolic function generator. An output of the hyperbolic function generator is connected to a counter-indicator unit. Both outputs of the input command flip-flop are electrically coupled to the leadout of the standard capacitor via charging or discharging circuits. The hyperbolic function generator includes, according to the invention, a controlled pulse generator with a linear modulation characteristic, whose input is the control input of the hyperbolic function generator, as well as a start-stop circuit whose first input is connected to the output of the controlled pulse generator, whose second input is connected to the command input of the hyperbolic function generator, and whose output is connected to the output of the hyperbolic function generator.

It is preferred that the start-stop circuit should include a first switch whose command input is connected to the second input of the start-stop circuit and whose signal input is connected to the first input of the start-stop circuit; a second switch whose signal input is connected to an output, of the first switch; a third switch whose signal input is connected to the output of the first switch; a first flip-flop whose counting input is connected to an output of the second switch, whose command input is connected to the command input of the first switch, whose "0" output is connected via a first diode to a command input of the third switch, and whose "1" output is connected to the command input of the second switch; a second flip-flop whose counting input is connected to an output of the third switch, whose command input is connected to the command input of the first switch, and whose "1" output is connected via a second diode to the command input of the third switch; and a third flip-flop whose first input is connected to the "1" output of the first flip-flop, whose second input is connected to the "1" output of the second flip-flop, whose command input is connected to the command input of the first switch, and whose output is connected to the output of the start-stop circuit.

In an alternate embodiment, it is preferable that the start-stop circuit should include a first flip-flop whose counting input is connected to the first input of the start-stop circuit, and whose output is connected to the output of the start-stop circuit; and a second flip-flop whose command input is connected to the second input of the start-stop circuit, whose counting input is connected to the output of the first flip-flop and to the output of the start-stop circuit, and whose output is connected to a command input of the first flip-flop.

It is preferable that the counter-indicator unit should comprise an output switch whose command input is connected to an input of the counter-indicator unit and whose output is connected to an input of a binary decade counter; and a reference frequency generator intended to fill in the time interval in the operation of the output switch with a series of pulses having a constant repetition rate, an output of said generator being connected to a signal input of the output switch.

The proposed device for digitally measuring instantaneously parameter values of slowly changing processes substantially reduces the time of measurements and analysis and produces results in the units of the parameter being measured, which are functionally related to the frequency. The device also makes it possible to carry out measurements in a broad dynamic range.

Other objects and advantages of the present invention will become more apparent from the following detailed description of preferred embodiments thereof taken in conjunction with the accompanying drawings, wherein:

FIG. 5 ($a, b, c, d, e, f, g, h, i, j, k$) shows time plots related to the outputs of the components of the alternate embodiment of the device in accordance with the invention.

Figure 1:
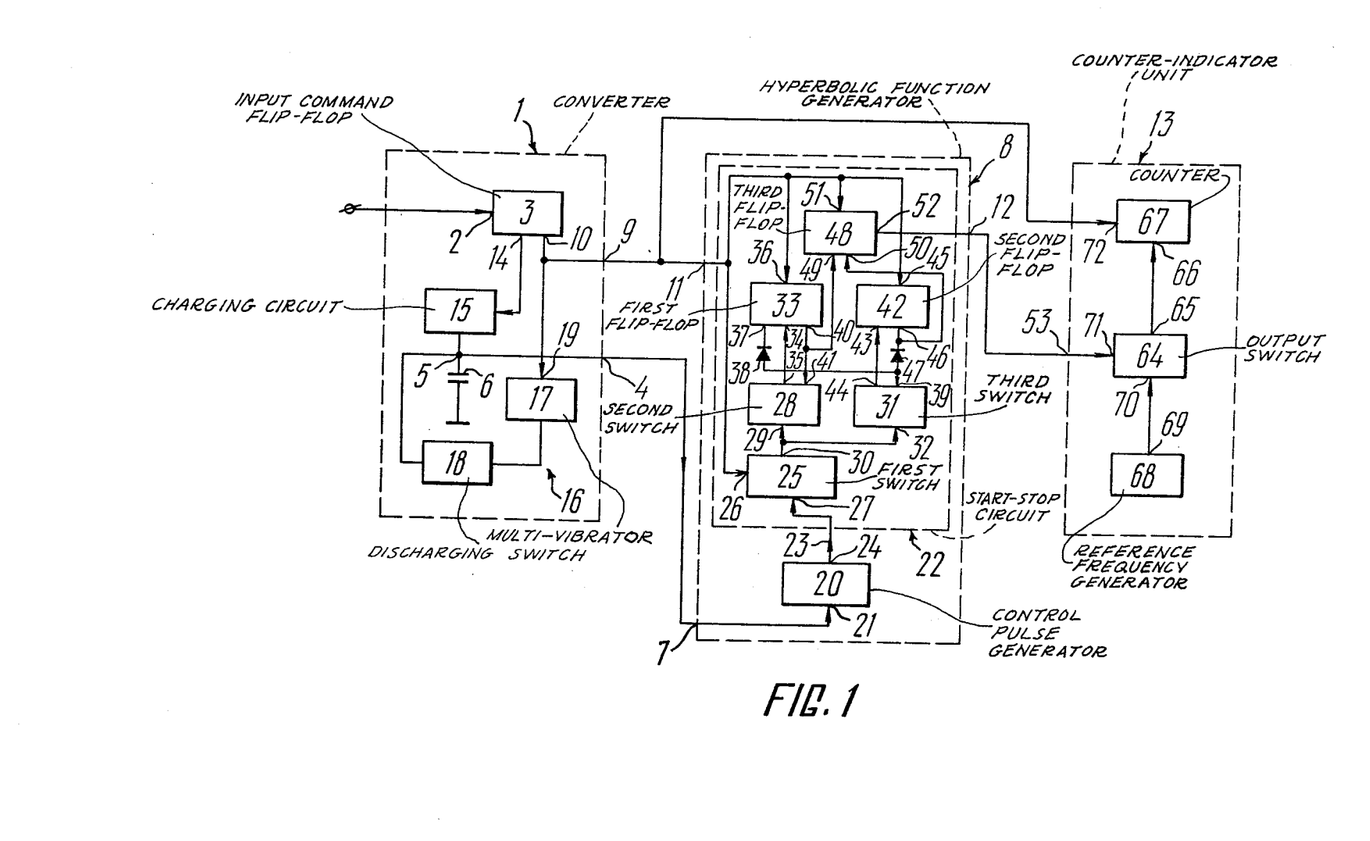
FIG. 1 is a block diagram of a device for digitally measuring parameter values of slowly varying processes, in accordance with the invention.

Referring now to the attached drawings, the proposed device for measuring parameter values of slowly changing processes comprises a time-to-voltage converter f1 (FIG. 1). A counting input 1 of an input command flip-flop 3 of the converter 1 is the input of the device. A first output 4 of the converter 1, which is a leadout 5 of a standard capacitor 6, is connected to a control input 7 of a hyperbolic function generator 8. A second output 9 of the converter 1, which is a first output 10 of the input command flip-flop 3, is connected to a command input 11 of the hyperbolic function generator 8. An output 12 of the hyperbolic function generator is connected to a counter-indicator unit 13. A second output 14 of the command flip-flop 3 is electrically coupled to the leadout 5 of the standard capacitor 6 via a charginc circuit 15. In the embodiment under review, the circuit 15 is a generator whose circuitry is that of a voltage-to-current converter built with an operational amplifier. The first output 10 of the command flip-flop 3 is electrically coupled to the leadout 5 of the standard capacitor 6 through a discharging circuit 16. In the embodiment under review, the circuit 16 includes a single-shot multivibrator 17 and a discharging switch 18, which are connected in series. The first output 10 of the command flip-flop 3 is connected to an input 19 of the single-shot multivibrator 17. The circuitry of the multivibrator 17 can be any one of the known circuits for such a device. (cf. "Impulsnye schemy na poluprovodnikovykh priborakh. Proyektirovaniye i raschyot" "Pulse Circuits of Semiconductor Instruments. Designs and Calculations", ed. by Ye. I. Galperin and I. P. Stepanenko, Sovietskoye Radio Publishers, Moscow, 1970, p. 98).

The hyperbolic function generator 8 comprises a controlled pulse generator 20 with a linear modulation characteristic, whose input 21 is the control input 7 of the hyperbolic function generator 8. The hyperbolic function generator further includes a start-stop circuit 22 whose first input 23 is connected to an output 24 of the generator 20. The output of the start-stop circuit 22 is connected to the output 12 of the hyperbolic function generator 8.

The start-stop circuit 22 comprises a first switch 25 whose command input 26 is connected to the command input 11 of the hyperbolic function generator 8, which is connected to the first output 10 of the input command flip-flop 3. A signal input 27 of said first switch 25 is connected to the output 24 of the controlled pulse generator 20.

The start-stop circuit 22 further comprises a second switch 28 whose signal input 29 is connected to an output 30 of the first switch 25. A third switch 31 of the start-stop circuit 22 has its signal input 32 connected to the output 30 of the first switch 25. A first flip-flop 33 of the start-stop circuit 22 has its counting input 34 connected to an output 35 of the command switch 28. A second input 36 of the flip-flop 33 is connected to the command input 11 of the hyperbolic function generator 8. A "0" output 37 of the first flip-flop 33 is connected via a first diode 38 to a command input 39 of the third switch 31. A "1" output 40 of the first flip-flop 33 is connected to a command input 41 of the second switch 28.

A second flip-flop 42 of the start-stop circuit 22 has its counting input 43 connected to an output 44 of the third switch 31. A command input 45 of the second flip-flop 42 is connected to the command input 11 of the hyperbolic function generator 8. A "1" output 46 of the second flip-flop 42 is connected via a second diode 47 to the command input 39 of the third switch 31.

A third flip-flop 48 of the start-stop circuit 22 has its first input 49 connected to the "1" output 40 of the first flip-flop 33, and its second input 50 connected to the "1" output 46 of the second flip-flop 42. A command input 51 of the third flip-flop 48 is connectd to the command input 11 of the hyperbolic function generator 8. An output 52 of the third flip-flop 48 is connected to the output of the start-stop circuit 22, which is connected to an input 53 of the counter-indicator unit 13.

According to an alternative embodiment of the start-stop circuit 22 (FIG. 2), the circuit 22 comprises a first flip-flop 54 whose counting input 55 is connected to a first input 56 of the start-stop circuit 22 and whose output 57 is connected to the output of the start-stop circuit 22. A second flip-flop 58 of the start-stop circuit 22 has a command input 59 which is connected to a second input 60 of the start-stop circuit 22, which is the command input of the hyperbolic function generator, and a counting input 61 which is connected to the output 57 of the first flip-flop 54 and to the output of the start-stop circuit 22. An output 62 of the second flip-flop 58 is connected to a command input 63 of the first flip-flop 54.

The counter-indicator unit 13 of the proposed device comprises an output switch 64 whose output 65 is connected to a first input 66 of a binary decade counter 67. The unit 13 further includes a reference frequency generator 68 intended to fill in the time intervals in the operation of the output switch 64 with a series of pulses having a constant repetition rate. An output 69 of the generator 68 is connected to a signal input 70 of the output switch 64. A command input 71 of the output switch 64 is connected to the input 53 of the counter-indicator unit 13.

The second output 9 of the converter 1 is also connected to a second input 72 of the binary decade counter 67 to erase the previous count.

Figures 3, 5A, 5K:
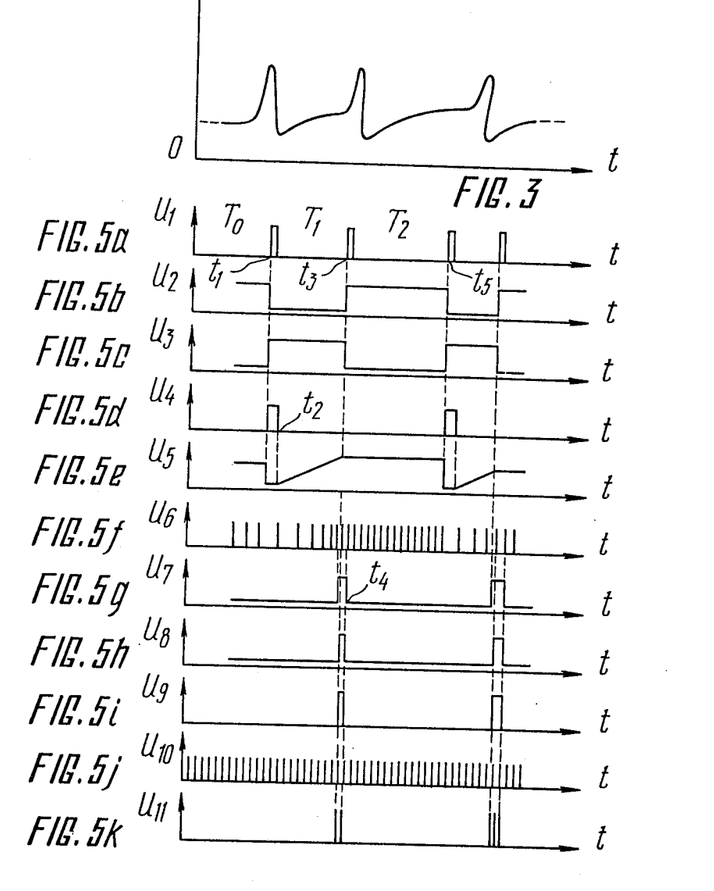
FIG. 3 is a time plot of a slowly changing process whose parameters are to be measured.

FIG. 3 is a time plot of a slowly changing process whose parameters are to be measured.

For better understanding of the operation of the proposed device, FIG. 4 shows time plots of a sequence of signals at the input of the proposed device. FIG. 4a is a signal at the output of the device; FIG. 4b is a signal at the output 10 of the input command flip-flop 3; FIG. 4c is a signal at the output 14 of the input command flip-flop 3; FIG. 4d is a signal at the output of the single-shot multivibrator 17; FIG. 4e is voltage across the standard capacitor 6; FIG. 4f is a sequence of pulses at the output 24 of the controlled pulse generator 20; FIG. 4g is a sequence of pulses at the output 30 of the first switch 25; FIG. 4h is a signal at the output 35 of the second switch 28; FIG. 4i is a signal at the output 44 of the third switch 31; FIG. 4j is a signal at the 1 output 40 of the first flip-flop 33; FIG. 4k is a signal at the 1 output 46 of the second flip-flop 42; FIG. 4l is a signal at the output 52 of the third flip-flop 48; FIG. 4m is a signal at the output 65 of the output switch 64 of the counter-indicator unit 13; FIG. 4n is a sequence of pulses at the output 69 of the reference frequency generator; and FIG. 4o is a sequence of pulses at the input 66 of the binary decade counter 67.

FIG. 5 shows time plots of a sequence of signals at the outputs of the units of the alternate embodiment of the proposed device. FIG. 5a shows input pulses; FIG. 5b is a signal at the output 10 of the input command flip-flop 3; FIG. 5c is a signal at the output 14 of the input command flip-flop 3; FIG. 5d shows output pulses at the output of the single-shot multivibrator 17; FIG. 5e is voltage across the standard capacitor 6; FIG. 5f is a sequence of pulses at the output 24 of the controlled pulse generator 20; FIG. 5g is a signal at the output 62 of the second flip-flop 58; FIG. 5h is a signal at the output 57 of the first flip-flop 54; FIG. 5i is a signal at the output 65 of the output switch 64 of the counter-indicator unit 13; FIG. 5j is a sequence of pulses at the output 69 of the reference frequency generator 68; and FIG. 5k is a sequence of pulses at the input 66 of the binary decade counter 67.

For better understanding of the operating principle of the device in accordance with the invention, consider some simplified theory.

Generally speaking, the instantaneous parameters are parameters M inversely (hyperbolically) related to the period T of a process, i.e.

$$M = D/T. \tag{1}$$

where M is the instantaneous parameter (frequency, speed, etc.),
T is the period of the process, and
D is the measurement base (the measurement interval, or the extension of the measurement area).

If we measure instantaneous frequency, equation (1) is expressed as follows:

$$F = D_1/T, \tag{2}$$

where F is the instantaneous frequency (the number of oscillations per time interval), and
$D_1$ is the measurement base.

For example, if we measure the instantaneous pulse rate value of a patient, $$F = 60/T, \tag{3}$$

because in medicine $D_1$ is equal to 60 seconds (one minute), and the count is made in terms of beats per minute.

For instantaneous speed measurements, equation (1) is expressed as follows:

$$V = D_2/T. \tag{4}$$

where
V is the instantaneous speed of a process (a number of distance units per time interval),
$D_2$ is the distance, and
T is the duration of the process over that distance $D_2$.

The first phase of the measuring cycle is storing the period of the process, for which purpose the standard capacitor is linearly charged during the period of time T, i.e.

$$U = KT, \tag{5}$$

where
U is the voltage across the reference capacitor, and
K is the proportionality factor.

Voltage U is then applied to the input of the controlled pulse generator with a linear modulation characteristic whose frequency is related to U by the formula:

$$F_o = K_1 \cdot U.$$

Substituting here the value of U from equation (5), we have:

$$F_{10} = K_1 U = K_1 KT, \tag{6}$$

where
$F_{10}$ is the frequency of the series of pulses at the output of the controlled pulse generator; and
$K_1$ is the proportionality factor.

The start-stop circuit discriminates the period of the controlled pulse generator, which is done by the formula:

$$T_{10} = (1/F_{10} = 1/K_1KT. \tag{7}$$

Expressing T in terms of equations (2) and (4), we have the following versions of (7):
for measuring instantaneous frequency $$T_{10} = (1/K_1KT) = F/K_1KD_1; \tag{8}$$

for measuring instantaneous speed $$T_{10} = (1/K_1KT) = V/K_1KD_2. \qquad (9)$$

In digitally measuring instantaneous values of parameters, it is most convenient to have the final result in digital form, i.e. the number of pulses arriving at the counter-indicator unit must be quantitatively equal to the parameter being measured and expressed in units commonly used by those working in the field.

During the period of time $T_{10}$ from the reference frequency generator to the counter there is applied a sequence of pulses N having a frequency f, i.e.

$$N = f \cdot T_{10}K_2 = MK_2, \qquad (10)$$

where M is the number of pulses arriving at the input of the counter;
f is the pulse frequency of the reference frequency generator; and
$K_2$ is the dimensional factor.

Substituting into equation (10) the values of $T_{10}$ from equations (8) and (9), we have:
for measuring instantaneous frequency $$N = f \cdot F \cdot K_2/K \cdot K_1 \cdot D_1; \qquad (11)$$

for measuring instantaneous speed $$N = f \cdot V \cdot K_2/K \cdot K_1 \cdot D_2. \qquad (12)$$

Thus, frequency is calculated from equation (11) by the formula:

$$F = K \cdot K_1 \cdot D_1/(f \cdot K_2) \cdot N. \qquad (13)$$

Similarly, speed is calculated from equation (12) by the formula:

$$V = K \cdot K_1 \cdot D_1/(f \cdot K_2) \cdot N. \qquad (14)$$

The values of the parameters F and V being measured are quantitatively equal to the number of pulses N, hence:

$$K \cdot K_1 \cdot D/(f \cdot K_2) = 1 \qquad (15)$$

From equation (15) it is easy to determine the frequency of the reference frequency generator for each specific measurement, i.e.:

$$f = K \cdot K_1 \cdot D/K_2. \qquad (16)$$

The dimensions and value of the factor $K_2$ of equation (16) are determined by the formula:

$$K_2 = K \cdot K_1 \cdot D/f. \qquad (17)$$

The device of the present invention operates as follows.

To the input 2 (FIG. 1) of the command flip-flop 3 there are applied input pulses $U_1$ (FIG. 4a) corresponding to the extremes of the slowly varying process of FIG. 3.

Figures 4A, 4B, 4C, 4D:
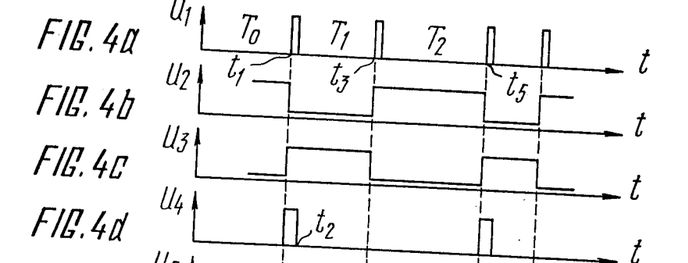
FIG. 4 ($a, b, c, d, e, f, g, h, i, j, k, l, m, n, o$) shows time plots related to the outputs of the components of the device in accordance with the invention.
Figures 4E, 4F:
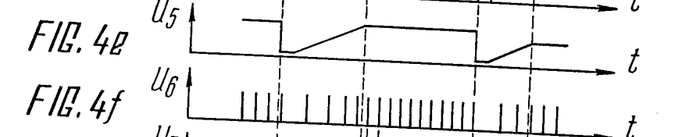

Upon the arrival of the first pulse $U_1$ (FIG. 4a) at the input 2 (FIG. 1) of the command flip-flop 3, which operates in the counting mode, the flip-flop 3 assumes a state where there is a "1" at its second output 14 (FIG. 4c) and a "0" at its first output 10 (FIG. 4b). The single-shot multivibrator is actuated, and at its output there appears a pulse $U_4$ (FIG. 4d) of a small duration, which acts upon the discharging circuit 18 (FIG. 1) and brings about a discharge of the previously charged standard capacitor 6. After the action of the discharge pulse has ceased, the standard capacitor 6 is linearly charged, as shown by $U_5$ (FIG. 4e) through the controlled current source 15 (FIG. 1) which is actuated at moments of time $t_1$ and $t_5$ (FIG. 4a) by a signal from the second output 14 (FIG. 1) of the flip-flop 3.

Upon the arrival of the second input pulse $U_1$ (FIG. 4a) at the time instant $t_3$, the input command flip-flop 3 assumes a state where at its second output 14 there is a "0" and at its first output 10 there is a "1". At this moment the standard capacitor, which had been linearly charging according to the formula:

$$U_5 = KT,$$

stops being charged. As this takes place, the standard capacitor stores the value of the period $T_1$.

Voltage from the standard capacitor 6 is applied to the input 21 of the controlled pulse generator 20 with a linear modulation characteristic. As a result, at the control pulse generator's output 24 there appears a sequence of pulses $U_6$ (FIG. 4f) which is related to the voltage across the standard capacitor 6 (FIG. 1).

$$F_{U_6} = K_1 \cdot U_5.$$

Substituting in this formula the value of $U_5$, we have:

$$F_{U_6} = K_1 KT.$$

The voltage across the standard capacitor 6 remains practically constant from the time instant $t_3$ till the time instant $t_5$; hence, from the time instant $t_3$ at the output 24 of the controlled pulse generator 20 there is set a constant repetition frequency of pulses $U_6$ (FIG. 4f), which is proportional to the previous period $T_1$.

From the output 24 (FIG. 1) of the controlled generator 20, the sequence of pulses $U_6$ is applied to the input 27 of the first switch 25 of the start-stop circuit 22. At the moment of time $t_3$ at the output 30 of the switch 25 there appears a sequence of pulses $U_7$ (FIG. 4g) having a constant repetition rate.

Figures 4G, 4H:
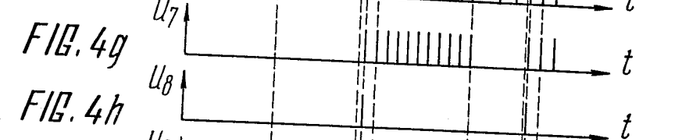
Figures 4I, 4J:
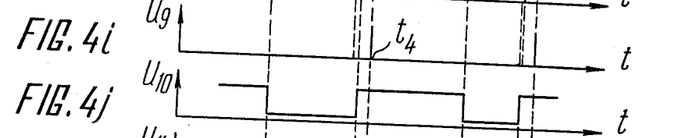
Figures 4K, 4L:
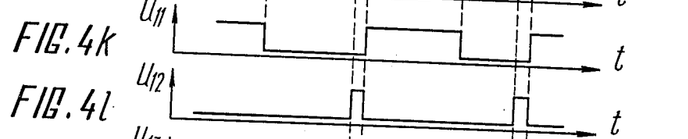
Figures 4M, 4N, 4O:
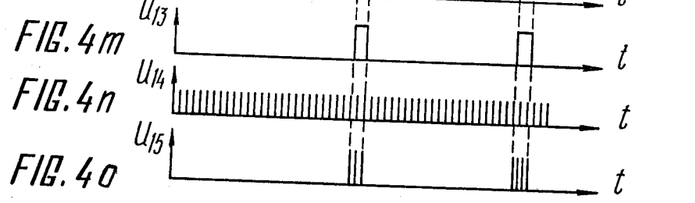

At the moment of time $t_1$ the flip-flop 33 (FIG. 1), 42 and 48 are set so that at the output 40 of the flip-flop 33 there is a "0", i.e. the signal $U_{10}$ (FIG. 4j), the output 46 (FIG. 1) of the flip-flop 42 there is a "0", i.e. the signal $U_{11}$ (FIG. 4k), and at the output 52 (FIG. 1) of the flip-flop 48 there is a "0", i.e. the signal $U_{12}$ (FIG. 4l).

As a result, at the time instant $t_3$ the second switch 28 is conducting, whereas the third switch 31 is not conducting.

At the time instant $t_3$ the first switch 25 is driven into conduction, and from its output 30 the first pulse $U_8$ (FIG. 4h) of the sequence of pulses $U_7$ (FIG. 4g) is applied via the second conducting switch 28 to the input 34 of the first flip-flop 33. As this takes place, the first flip-flop 33 assumes a state where there is a "1" at its output 40. Simultaneously, this voltage drop acts on the input 4l of the switch 28 and renders it non-conducting. Said voltage drop also acts on the input 49 of the third flip-flop 48; as a result, the flip-flop 48 assumes a state where at its output 52 there is a "1", i.e. the signal $U_2$ (FIG. 4l).

At the moment of time $t_3$ the third switch 31 (FIG. 1) is rendered non-conducting by signals from the output 37 of the first flip-flop 33 and the output 46 of the second flip-flop 42, which are applied to the command input 39 of the switch 31 via the coincidence circuit built of the diodes 38 and 47. The first pulse, which passes through the second switch 28 at the time instant $t_3$, renders said second switch 28 non-conducting, sets the output 40 of the first flip-flop 33 into the "1" state and drives the third switch 31 into conduction by means of its command input 39. The second pulse $U_9$ (FIG. 4i) is applied via the third switch 31 to the input 43 of the second flip-flop 42, said pulse $U_9$ belonging to the sequence of pulses $U_7$ (FIG. 4g). As this takes place, the second flip-flop 42 (FIG. 1) assumes a state where there is "1" at its output 46. By means of a signal from the output 46 of the second flip-flop 42, which acts on the input 39 of the third switch 31 via the diode 47, the third switch 31 is rendered non-conducting.

At the same time, the signal from the output 46 of the second flip-flop 42 acts on the second input 50 of the third flip-flop 48 so that the third flip-flop's output 52 is again set to zero. As a result, at the output 52 of the flip-flop 48 there appears the voltage drop $U_{12}$ (FIG. 4l) whose duration is equal to the time span between the first and second pulses of the sequence of pulses $U_7$ (FIG. 4g), i.e. the duration of the output pulse of the third flip-flop 48 (FIG. 1) being equal to the repetition frequency of pulses from the output 24 of the controlled pulse generator 20. The frequency of the generator 20 is determined by the formula:

$$F_{U_6} = K_1 \cdot K \cdot T,$$

hence, $$T_{U_6} = 1/K_1 \cdot K \cdot T.$$

Thus, the duration of the pulse at the output 12 of the hyperbolic function generator 8 is inversely (hyperbolically) related to the period of the process being analyzed.

Figure 2:
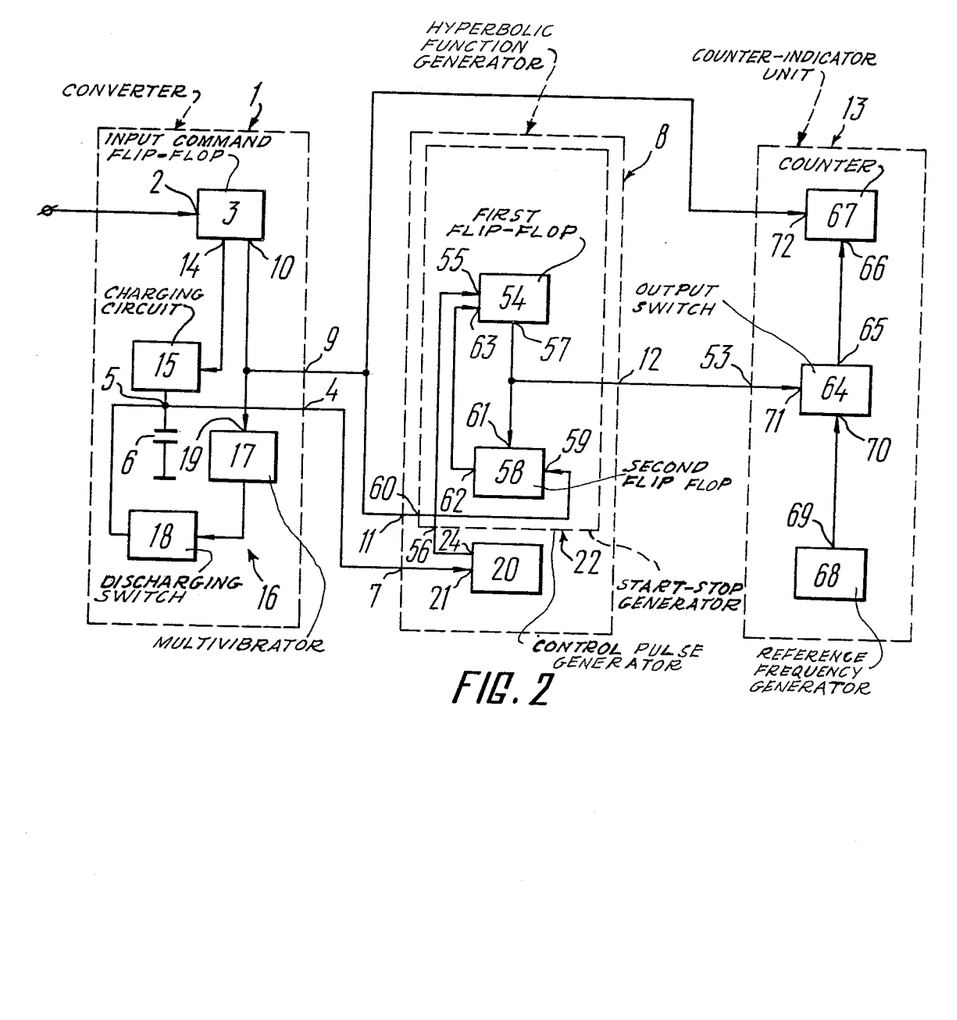
FIG. 2 is a block diagram showing another embodiment of the start-stop circuit of the device in accordance with the invention.

If the hyperbolic function generator 8 employs the embodiment of the start-stop circuit 22 shown in FIG. 2, the device operates as described above until the time instant $t_3$.

At the time instant $t_3$, the voltage $U_5$ (FIG. 5e) is applied from the standard capacitor 6 (FIG. 2) to the input 21 of the controlled pulse generator 20 having a linear modulation characteristic. From the output 24 of the controlled pulse generator 20, the pulses $U_6$ (FIG. 5f), having a repetition rate which is proportional to the voltage across the standard capacitor 6 (FIG. 2) are applied to the count input 55 of the first flip-flop 54 of the start-stop circuit 22.

At the time instant $t_3$, from the first output 10 of the input command flip-flop 3 the signal is applied via the command input 11 of the hyperbolic function generator 8 to the command input 59 of the second flip-flop 58 of the start-stop circuit 22.

The second flip-flop 58 assumes a state where its output 62 has a "1", i.e. the signal $U_7$ (FIG. 5g); the first flip-flop 54 (FIG. 2) can now operate in the counting mode. The first pulse of the controlled generator 20, which is applied to the count input 55 of the first flip-flop 54 after the inhibit signal has been removed from its command input 63, after the moment of time $t_3$ sets the first flip-flop 54 into a state where at its output 57 there is a "1", i.e. the signal $U_8$ (FIG. 5h).

The second pulse of the controlled generator 20 (FIG. 2), which is applied to the count input 55 of the first flip-flop 54 after the inhibit signal has been removed from the command input 63 of the flip-flop 54, again sets the first flip-flop 54 into a state where its output 57 is again set to zero. This takes place at the moment of time $t_4$.

Simultaneously, the signal from the output 57 of the first flip-flop 54 is applied to the output 12 of the hyperbolic function generator 8 and the input 61 of the second flip-flop 58, at the time instant $t_4$ the second flip-flop 58 assuming a state when its output 62 is again set to zero.

As in the case of the embodiment of FIG. 1, the duration of the pulse across the output 12 of the hyperbolic function generator 8 is inversely (hyperbolically) related to the period of the process being analyzed.

In the course of duration of said output pulse $U_9$ (FIG. 5i), which is applied to the input 71 (FIG. 2) of the output output switch 64 of the counter-indicator unit 13, the switch 64 is driven into conduction, so that from the reference frequency generator 68 to the input 66 of the counter 67 there arrives the sequence of pulses $U_{10}$ (FIG. 5j) which is quantitatively equal to the parameter of the slowly changing process being analyzed.

Upon the arrival of the second signal $U_1$ (FIG. 4a), the binary decade counter 67 is reset by a signal from the first output 10 of the input command flip-flop 3. As a result, it is again possible to enter a new value in the counter 67.

The proposed device for digitally measuring parameter values of slowly changing processes employs a limited quantity of generally known integrated-circuit units. The use of the proposed device in measuring instruments substantially reduces the time required for measurements and analysis and makes it possible to connect the measuring instruments to a computer, which is another step towards developing automatic control systems intended to suit different purposes. A major advantage of the device according to the invention is, the fact that it produces the results in units of the parameter being measured, which are functionally related to frequency, for example, impacts per minute, liters per hour, centimeters per second, kilometers per hour, revolutions per minute, etc.

What is claimed is:

1. A digital device for measuring instantaneous parameter values of slowly varying processes, comprising:
    a time-to-voltage converter having an input, a first output and a second output;
    an input command flip-flop of said converter having two outputs and
    a counting input which is connected to the input of the converter and to an input of the device, a first of said outputs being connected to said second output of said converter;
    a capacitor of said converter having
    a leadout connected to said first output of said converter;
    a charging circuit having an input connected to said second output of said input command flip-flop and an output connected to said leadout of said capacitor;
    a discharging circuit having an input connected to a first output of said input command flip-flop and an output connected to said leadout of said capacitor;
    a hyperbolic function generator having
    a control input connected to said leadout of said capacitor and
    a command input connected to said second output of said converter;

a controlled pulse generator, with a linear modulation characteristic of said hyperbolic function generator, having
an input connected to the control input of said hyperbolic function generator;
a start-stop circuit of said hyperbolic function generator having
a first input connected to an output of said pulse generator,
a second input connected to the command input of said hyperbolic function generator, and
an output connected to the output of said hyperbolic function generator; and
a counter-indicator unit having an input connected to said output of said hyperbolic function generator.

2. A device as claimed in claim 1, wherein the start-stop circuit comprises:
a first switch having an output,
a command input connected to said second input of said start-stop circuit and
a signal input connected to said first input of said start-stop circuit;
a second switch having a signal input connected to said output of said first switch, a command input and an output;
a third switch having a signal input connected to said output of said first switch, a command input and an output;
a first flip-flop having a counting input connected to said output of the second switch,
a command input connected to said second input of said start-stop circuit,
a "0" output connected via a first diode to said command input of said third switch, and
a "1" input connected to said command input of said second switch;
a second flip-flop having a counting input connected to said output of said third switch,
a command input connected to said second input of said start-stop circuit,
a "1" output connected via a second diode to said command input of said third switch; and
a third flip-flop having a first input connected to said "1" output of said first flip-flop,
a second input connected to said "1" output of said second flip-flop,
a command input connected to said second input of said start-stop circuit, and
an output connected to said output of said start-stop circuit.

3. A device as claimed in claim 1, wherein the start-stop circuit comprises:
a first flip-flop having a control input connected to said first input of said start-stop circuit, a command input and an output connected to said output of the start-stop circuit;
a second flip-flop having a command input connected to said second input of said start-stop circuit,
a counting input connected to said output of said first flip-flop and to said output of the start-stop circuit, and
an output connected to said command input of said first flip-flop.

4. A device as claimed in claim 2, wherein said counter-indicator unit comprises:
an output switch having an output, a command input connected to said input of said counter-indicator unit and a signal input;

a binary decade counter having a first input connected to said output of said output switch and
a second input connected to said second output of said converter; and
a reference frequency generator, to fill in the time interval in the operation of said output switch with a series of pulses of a constant repetition frequency, having an output connected to said signal input of said output switch.

5. A device as claimed in claim 3, wherein said counter-indicator unit comprises:
an output switch having an output, a command input connected to said input of said counter-indicator unit and a signal input;
a binary decade counter having a first input connected to said output of said output switch, and
a second input connected to said second output of said converter; and
a reference frequency generator, to fill in the time interval in the operation of said output switch with a series of pulses of a constant repetition rate, having an output connected to said signal input of said output switch.

6. A device as claimed in claim 1, wherein said counter-indicator unit comprises:
an output switch having an output, a command input connected to said input of said counter-indicator unit and a signal input;
a binary decade counter having a first input connected to said output of said output switch, and
a second input connected to said second output of said converter; and
a reference frequency generator, to fill in the time interval in the operation of said output switch with a series of pulses of a constant repetition rate, having an output connected to said signal input of said output switch.

7. A device as claimed in claim 1, wherein said discharging circuit comprises:
a single shot multivibrator having an input connected to said input of said discharging circuit and an output;
and a discharging switch having an input connected to said output of said single shot multivibrator and an output connected to said output of said discharging circuit.

8. A device as claimed in claim 2, wherein said discharging circuit comprises:
a single shot multivibrator having an input connected to said input of said discharging circuit and an output;
and a discharging switch having an input connected to said output of said single shot multivibrator and an output connected to said output of said discharging circuit.

9. A device as claimed in claim 3, wherein said discharging circuit comprises:
a single shot multivibrator having an input connected to said input of said discharging circuit and an output;
and a discharging switch having an input connected to said output of said single shot multivibrator and an output connected to said output of said discharging circuit.

10. A device as claimed in claim 4, wherein said discharging circuit comprises:

a single shot multivibrator having an input connected to said input of said discharging circuit and an output;

and a discharging switch having an input connected to said output of said single shot multivibrator and an output connected to said output of said discharging circuit.

11. A device as claimed in claim 5, wherein said discharging circuit comprises:

a single shot multivibrator having an input connected to said input of said discharging circuit and an output;

and a discharging switch having an input connected to said output of said single shot multivibrator and an output connected to said output of said discharging circuit.

12. A device as claimed in claim 6, wherein said discharging circuit comprises:

a single shot multivibrator having an input connected to said input of said discharging circuit and an output;

and a discharging switch having an input connected to said output of said single shot multivibrator and an output connected to said output of said discharging circuit.

* * * * *